(12) United States Patent
Yokota et al.

(10) Patent No.: US 9,974,556 B2
(45) Date of Patent: May 22, 2018

(54) METHOD FOR INSERTING ENDOSCOPIC DEVICE INTO HOLLOW ORGAN USING GUIDE WIRE

(71) Applicant: OLYMPUS CORPORATION, Tokyo (JP)

(72) Inventors: Takuo Yokota, Hino (JP); Rei Matsunaga, Hino (JP); Kunihide Kaji, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 487 days.

(21) Appl. No.: 14/527,150

(22) Filed: Oct. 29, 2014

(65) Prior Publication Data

US 2016/0121084 A1    May 5, 2016

(51) Int. Cl.
A61B 17/29 (2006.01)
A61M 25/09 (2006.01)
A61F 2/966 (2013.01)
A61B 17/00 (2006.01)
A61B 17/34 (2006.01)
A61F 2/04 (2013.01)

(52) U.S. Cl.
CPC .............. *A61B 17/29* (2013.01); *A61F 2/966* (2013.01); *A61M 25/09041* (2013.01); *A61B 17/3415* (2013.01); *A61B 17/3478* (2013.01); *A61B 2017/0034* (2013.01); *A61B 2017/00818* (2013.01); *A61F 2002/041* (2013.01)

(58) Field of Classification Search
CPC .... A61B 2017/00296; A61B 2017/003; A61B 17/29; A61B 17/00234; A61M 25/09
See application file for complete search history.

(56) References Cited

U.S. PATENT DOCUMENTS

| | | | | |
|---|---|---|---|---|
| 6,461,296 | B1* | 10/2002 | Desai | A61B 8/0841 600/210 |
| 2009/0054927 | A1* | 2/2009 | Agnew | A61B 17/0057 606/213 |
| 2010/0042077 | A1 | 2/2010 | Okada | |
| 2012/0203066 | A1* | 8/2012 | Okazaki | A61B 1/00087 600/114 |

FOREIGN PATENT DOCUMENTS

| | | |
|---|---|---|
| JP | A-2002-119514 | 4/2002 |
| JP | A-2002-253479 | 9/2002 |
| JP | A-2008-289556 | 12/2008 |

OTHER PUBLICATIONS

Dhir, Vinay et al., "EUS-Guided Biliary Rendezvous using a short hydrophilic guide wire," *J Interv Gastroenterol*, vol. 1 No. 4, pp. 153-159, (2011).

* cited by examiner

*Primary Examiner* — Timothy J Neal
(74) *Attorney, Agent, or Firm* — Oliff PLC

(57) ABSTRACT

In a disclosed method for inserting an endoscopic device, in a state in which a guide wire is inserted through an opening of a hollow organ of a subject, the guide wire is indwelt in the hollow organ. Next, a flexible endoscope is made to approach the opening of the hollow organ. Next, inside of the body of the subject, an endoscopic device that projects from the tip of a channel of the endoscope slidably engages with the guide wire. Next, the endoscopic device is inserted into the hollow organ through the opening, along the guide wire. The guide wire that is indwelt once is subsequently used as a guide for second and subsequent insertions of endoscopic devices.

5 Claims, 10 Drawing Sheets

METHOD FOR INSERTING ENDOSCOPIC DEVICE INTO HOLLOW ORGAN USING GUIDE WIRE

BACKGROUND OF THE INVENTION

Field of the Invention

The present invention relates to a method for inserting an endoscopic device into a hollow organ of a subject (such as a patient) using a guide wire. In particular, the present invention relates to an insertion method that is suitable for cases in which, for example, an endoscopic device is inserted into a hollow organ, such as the bile duct or the pancreatic duct, through an opening, such as the duodenal papilla.

Description of the Related Art

For diseases involving a hollow organ of the human body, an endoscopic device may be inserted into the hollow organ using a guide wire. This technique is often used in an endoscopic procedure performed in the bile and pancreatic regions. When this endoscopic procedure is performed, a guide wire is indwelt in a target hollow organ, such as the bile duct or the pancreatic duct. An endoscopic device is inserted into the hollow organ through the guide wire. A required procedure is then performed using the endoscopic device.

In this endoscopic procedure, a plurality of endoscopic devices are often typically used. In this instance, the endoscopic devices are required to be inserted and removed from the endoscope numerous times through the guide wire, each time the endoscopic device is exchanged. The insertion and removal operation requires a collaborative operation between an operator and an assistant. This collaborative operation places a significant load on the overall endoscopic procedure.

JP-A-2002-119514 discloses sending an endoscopic device along a guide wire to a target site within the body. However, because the endoscopic device is engaged with the guide wire outside of the body, the endoscopic device is required to be inserted and removed through the guide wire to exchange the endoscopic device.

SUMMARY

Therefore, it is desired that an insertion method be provided that, when an endoscopic device is inserted into a target hollow organ using a guide wire, does not require the endoscopic device to be inserted through the guide wire, does not require a collaborative operation with an assistant, and enables high work efficiency.

In a typical example, there is provided a method for inserting an endoscopic device into a hollow organ, including: a first step of indwelling, in a region in which a first hollow organ communicates with a second hollow organ via an opening in a body of a subject, a guide wire in the first hollow organ such that the guide wire is kept to be inserted through the opening; a second step of making a flexible endoscope approach the opening in the first hollow organ, the flexile endoscope being provided with a channel; a third step of slidably engaging an endoscopic device that projects from a tip of the channel of the endoscope with the guide wire inside the body of the subject; and a fourth step of inserting, along the guide wire, the endoscopic device into the first hollow organ through the opening.

Furthermore, preferably, the insertion method includes a fifth step of releasing the endoscopic device from engaging with the guide wire in the opening; a sixth step of releasing the indwelling object from the endoscopic device inserted in the opening; and a seventh step of pulling out the endoscopic device from the opening, with both the indwelling object and the guide wire indwelt in the first hollow organ.

DETAILED DESCRIPTION OF THE PREFERRED EMBODIMENTS

Various examples of a method for inserting an endoscopic device into a hollow organ of a subject (such as a patient) using a guide wire of the present invention will be described with reference to the drawings.

To perform this insertion method, a known flexible endoscope, and/or a known ultrasound endoscope or a known transabdominal ultrasound diagnostic apparatus that enables contact with an ultrasound probe from outside of the body are used. In addition, a known guide wire and a known endoscopic device, such as a catheter, that is inserted into a channel of the flexible endoscope are used.

First Example

First, a first example of the method for inserting an endoscopic device of the present invention and a variation example thereof will be described with reference to FIG. 1 to FIG. 3. The first example is based on a basic concept of the present invention.

Figure 1:
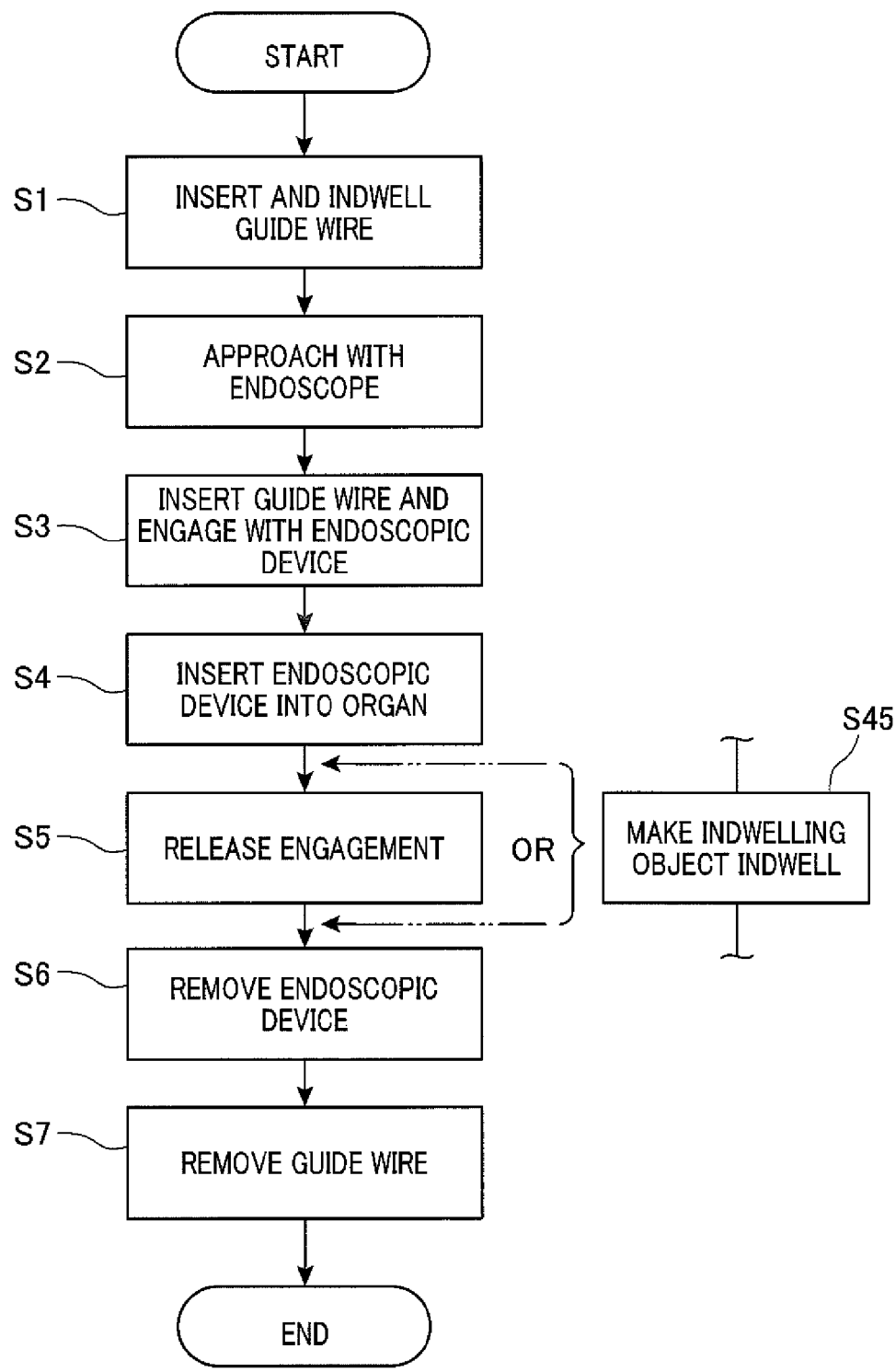
FIG. 1 is a flowchart for explaining a method for inserting an endoscopic device in a first example of the present invention.
Figure 2:
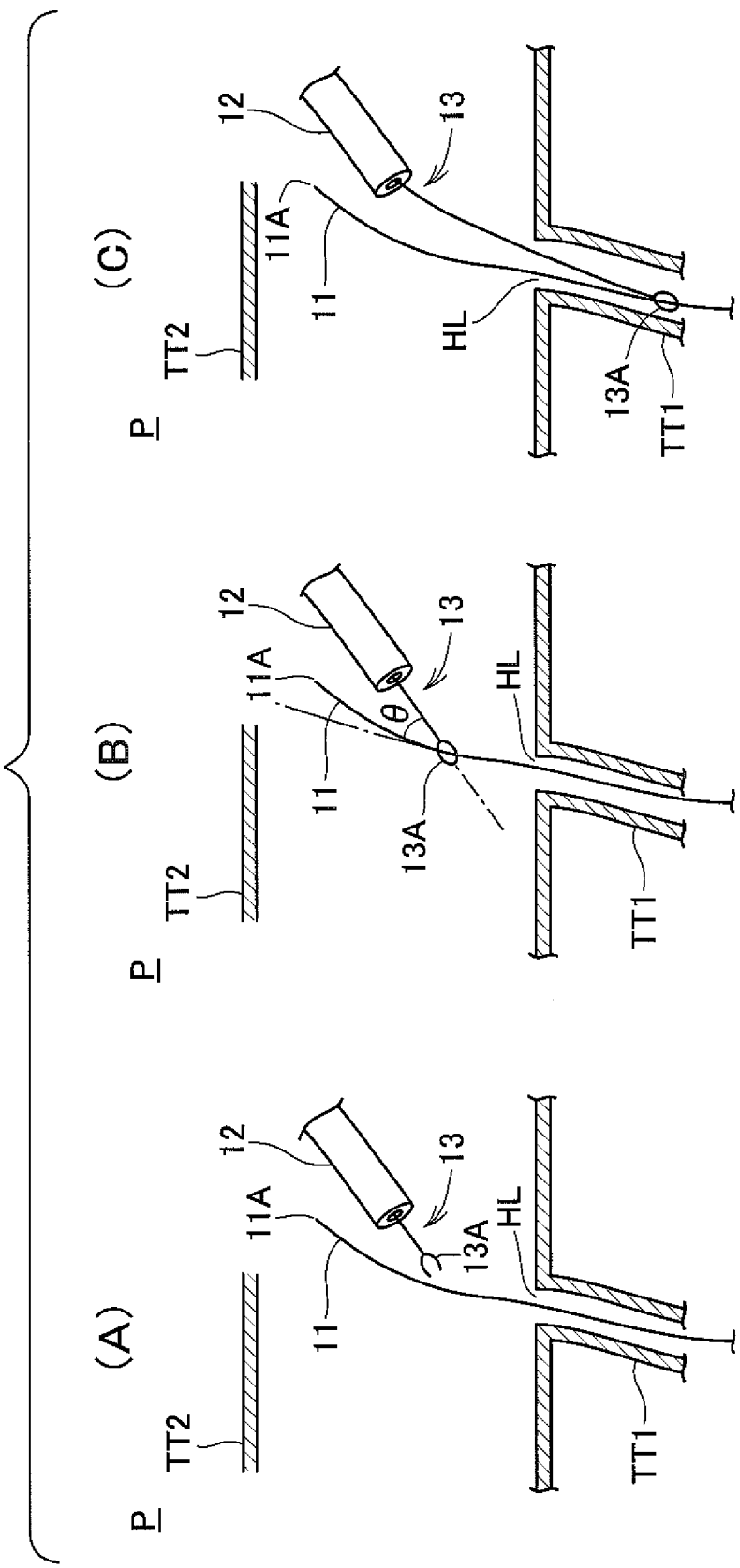
FIG. 2 is a diagram for explaining the insertion method in the first example.

FIG. 1 shows the operational procedure of the method for inserting an endoscopic device in the first example. As schematically shown in FIG. 2, the insertion method is applied to a region in a subject P in which an opening HL of a first hollow organ TT1 communicates with a second hollow organ TT2. In addition, in the region, the opening HL opens into the lumen of the second hollow organ TT2.

As shown in FIG. 1, at a first step S1, in a state in which a guide wire 11 is inserted through the opening HL in the subject P, the guide wire 11 is indwelt in the first hollow organ TT1 (see FIG. 2(A)). Here, the first hollow organ TT1 is the bile duct, the pancreatic duct, or a lesion such as a cyst. The second hollow organ TT2 is, for example, the duodenum, the stomach, or the small intestine. The opening HL is a papilla, an anastomotic site, or a puncture site. Indwelling of the guide wire 11 is performed through the gastrointestinal tract under an endoscope. Alternatively, the guide wire 11 is indwelt percutaneously from outside of the body.

Next, at the second step S2, an endoscopic device is inserted into a channel of a flexible endoscope 12 that is inserted into the second hollow organ TT2. The endoscopic device is made to approach the opening HL (see FIG. 2(A)). An endoscopic device 13 is, for example, grasping forceps. In this way, the endoscopic device 13 is preferably provided with a grasping portion 13A to slidably engage with the guide wire 11 at a subsequent step.

Next, the procedure advances to a third step S3. The endoscopic device 13 is projected from the tip of the channel of the endoscope 12. The endoscopic device 13 is then engaged with the guide wire 11 so as to slide freely (see FIG. 2(B)). The engagement is performed so that the grasping portion 13A of the endoscopic device 13 pinches the guide wire 11 at a midway position from an obliquely lateral direction. At this time, the midway portion of the guide wire 11 is pinched so that an angle formed by the length directions of both the guide wire 11 and the endoscopic device 23 is smaller than 90 degrees (acute angle). A reason for this is to facilitate entry of the tip of the endoscopic device 13 into the opening HL. Specifically, as described in FIG. 2(B), an angle formed by the axes in the length directions of both the guide wire 11 and the endoscopic device 23 when presumed that the guide wire 11 and the endoscopic device 23 are in a linear state is an appropriate acute angle that is at least 90 degrees or less. The angle is preferably as small as possible, taking into consideration facilitating smooth passage of the grasping portion 13A into the opening HL, along the guide wire 11.

When the above-described engagement is completed, the procedure advances to a fourth step S4. With the grasping portion 13A of the endoscopic device 13 at the head, the grasping portion 13A is pushed forward towards the opening HL. As a result, the grasping portion 13A of the endoscopic device 13 and the portion connected thereto pass through the opening HL, along the guide wire 11. The grasping portion 13A and the portion connected thereto are inserted into the first hollow organ TT1 (see FIG. 2(C)).

Next, the engagement of the endoscopic device 13 to the guide wire 11 is released in the first hollow organ TT1 (Step S5).

Here, a variation example can be provided. In other words, after the operation at Step S5 is completed, an indwelt object, such as a stent, can be indwelt through the endoscopic device 13, using the endoscopic device 13 itself as a guide (Step S45; refer to the step indicating the variation example in FIG. 1). In the variation example as shown in FIG. 1, Step S45 for indwelling may be performed after Step S5. In other words, indwelling of the indwelt object and release of engagement with the guide wire 11 may be interchanged depending on the procedure.

Figure 3:
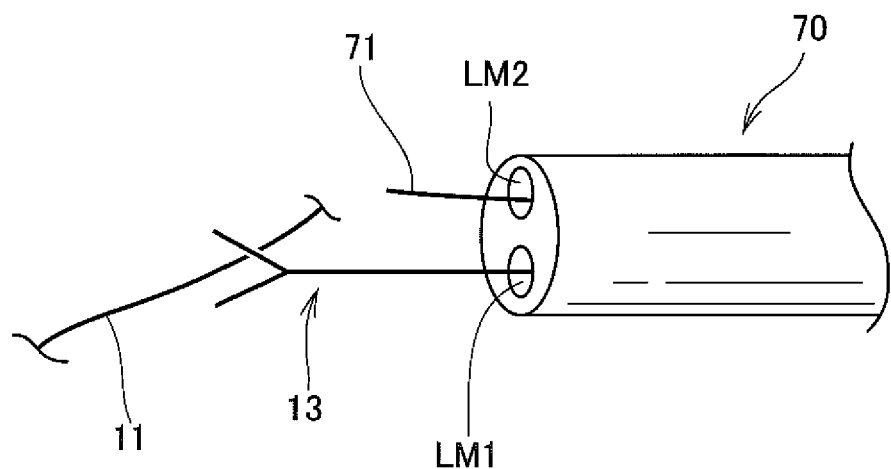
FIG. 3 is a diagram for explaining a variation example of the first example.

In addition, as another variation example, as shown in FIG. 3, the endoscopic device 13 may be used together with a guide sheath that has a plurality of lumens. FIG. 3 shows a tip portion of a guide sheath 70. The guide sheath 70 is positioned near the opening HL via the channel of the endoscope 12. Specifically, the endoscopic device 13 is used by being inserted into, for example, a first lumen LM1 of a plurality of lumens LM1 and LM2. When the guide sheath 70 is used, the tip portion of the guide sheath 70 is inserted into the first hollow organ TT1 with the insertion of the endoscopic device 13 in the process at Step S4. In this instance, after Step S4 or Step S5, Step S5, another guide wire 71 is inserted into the other second lumen LM2 of the plurality of lumens LM1 and LM2. The other guide wire 71 serves as an indwelt object. The tip portion of the guide wire 71 can be indwelt in the first hollow organ TT1 (such as the bile duct). Alternatively, a contrast agent can be injected into the bile duct or the like through the second lumen.

Subsequently, the endoscopic device 13 is removed from inside the body (Step S6). Furthermore, the guide wire 11 that has remained indwelt up to this time is removed (Step S7).

In this way, the endoscopic device is not required to be inserted and removed through the guide wire 11 to and from the outside of the body of the subject P. Therefore, the operation for inserting the endoscopic device is simplified and requires less time. In addition, a collaborative operation related to insertion that is performed between an operator and an assistant becomes unnecessary.

Second Example

Figure 4:
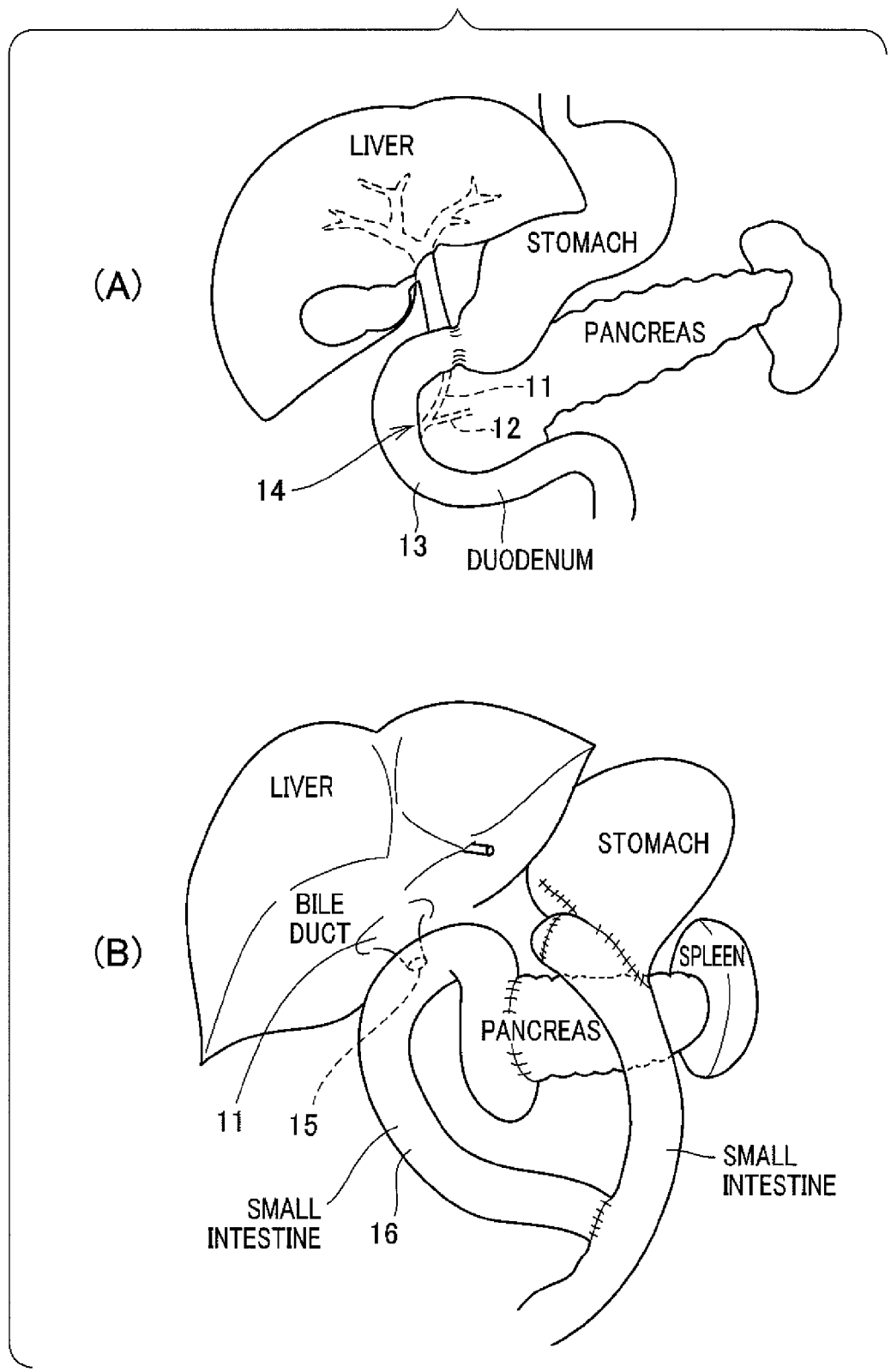
FIG. 4 is a diagram for explaining an anatomical example of a subject to which the method for inserting an endoscopic device in a second example of the present invention can be applied.

Next, the method for inserting an endoscopic device in a second example will be described with reference to FIG. 4 to FIG. 6.

In this example, a technique referred to as endoscopic retrograde cholangiopancreatography (ERCP) is applied to an anatomical example shown in FIG. 4(A). In this example, the first hollow organ is the bile duct 11 or the pancreatic duct 12. The opening is the duodenal papilla 14. The second hollow organ is the duodenum 13. Furthermore, as shown in FIG. 4(B), the technique can also be applied to an anatomical example in which a papilla is excised and the bile duct/pancreatic duct are connected by anastomosis with the small intestine, as in a patient after a pancreaticoduodenectomy. In this instance, the first hollow organ is the bile duct 11 or the pancreatic duct. The opening is an anastomotic site 15. The second hollow organ is the small intestine 16.

Figure 5:
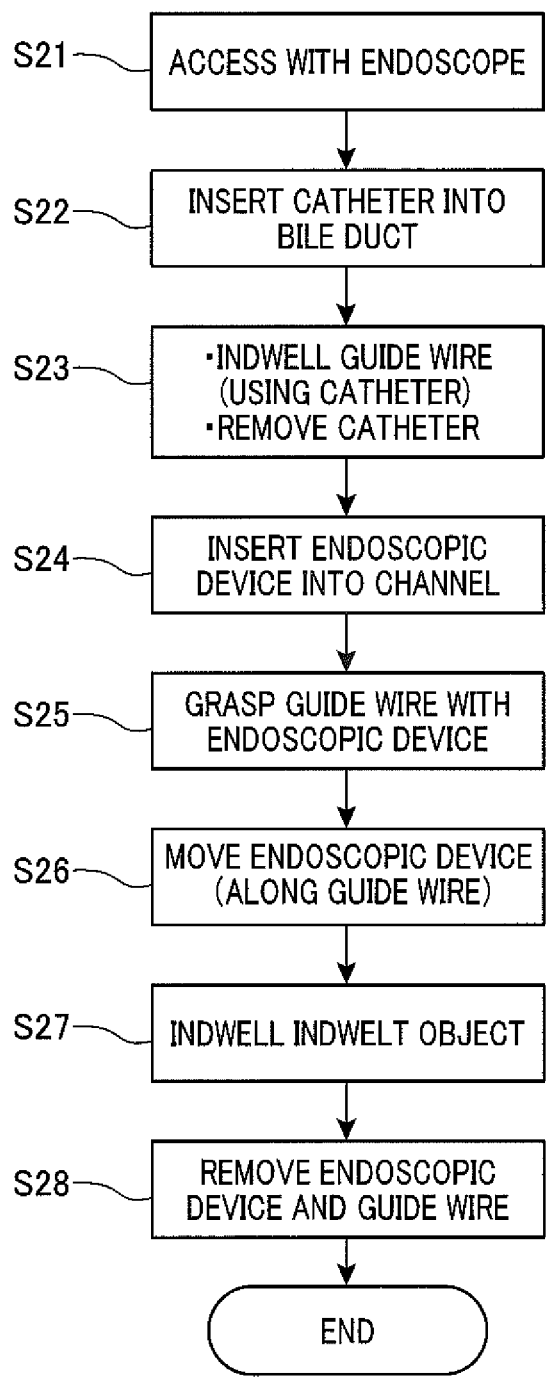
FIG. 5 is a flowchart for explaining the method for inserting an endoscopic device in the second example.
Figure 6:
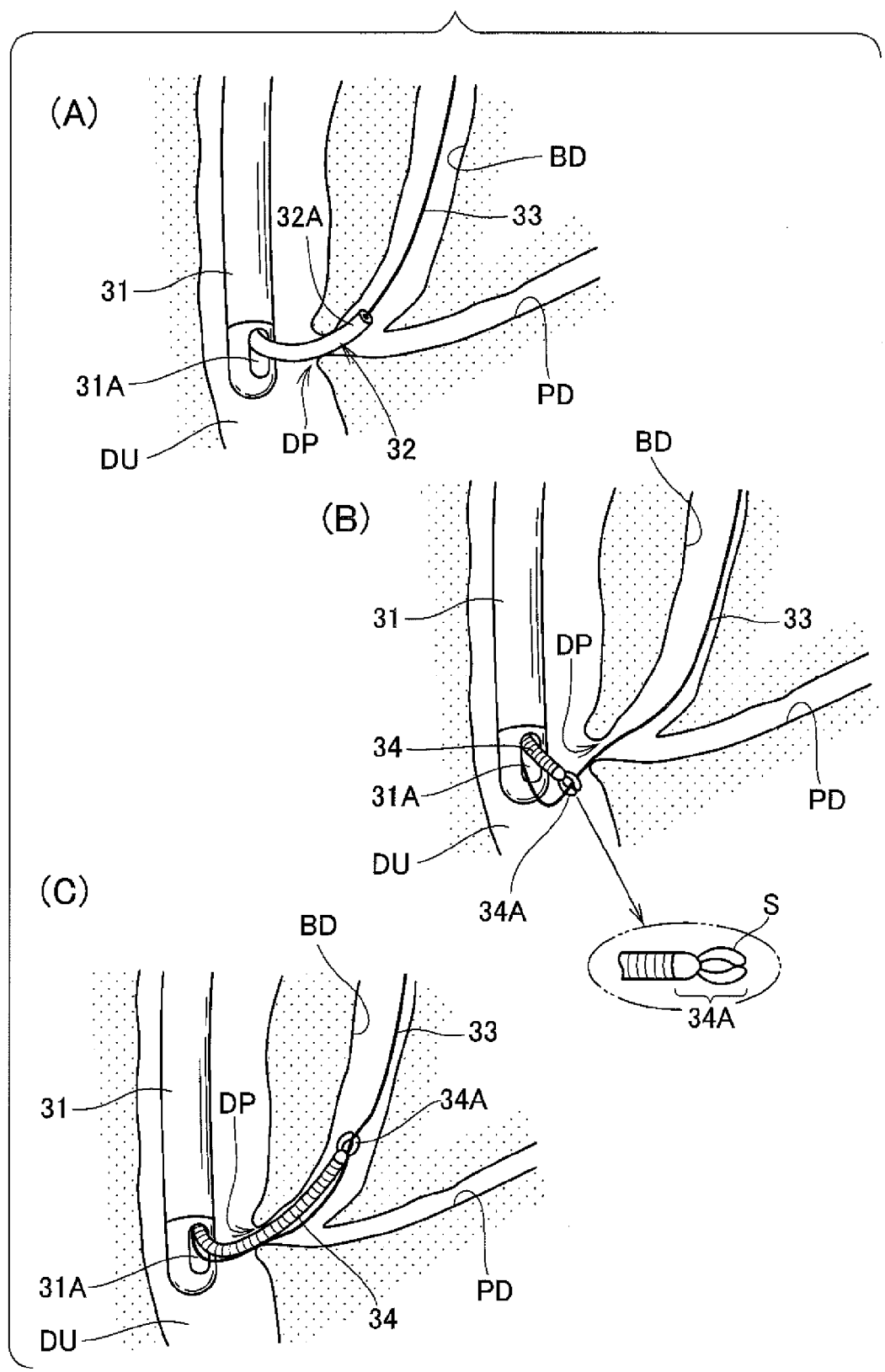
FIG. 6 is a diagram for explaining the insertion method in the second example.

First, the operator enables a flexible endoscope 31 for the duodenum to access the papilla DP of the duodenum D (FIG. 5, Step S21). In this state, the operator inserts a catheter 32 into a channel 31A of the endoscope 31. The operator projects a tip 32A of the catheter 32 from the opening of the channel 31A. In addition, the operator inserts the tip 32A into the bile duct BD, through the papilla DP (Step S22).

Next, the operator inserts a guide wire 33 into the catheter 32 from the base side of the endoscope 31 such that the tip of the guide wire 33 reaches the bile duct BD. The operator then indwells the guide wire 33 in the bile duct BD (Step S23; see FIG. 6(A)). After indwelling of the guide wire 33, the catheter 32 is removed. When there is only a single channel, the catheter 32 is required to be removed. However, if there are two channels, the removing step is not necessarily required. FIG. 6 shows an example in which there is a single channel. In FIG. 6, reference symbol PD represents the pancreatic duct.

Next, the operator inserts an endoscopic device 34, such as grasping forceps, into a channel 31A of the endoscope (Step S24).

Subsequently, the operator engages the endoscopic device 34 with the guide wire 33 by grasping the guide wire 33 with a grasping portion 34A of the endoscopic device 34 (Step S25; see FIG. 6(B)). The grasping portion 34A is formed at the tip of the endoscopic device 34. In a closed (meshed) state, both forceps portions at the tip side of the grasping portion 34A are in contact with each other. However, a space S is formed between the two forceps portions further toward the base side than the contacting portion. Therefore, the endoscopic device 34 is engaged with the guide wire 33 so that the guide wire 33 passes through the space S.

Next, the operator pushes forward the endoscopic device 34 along the guide wire 33 that is indwelt in the bile duct BD (Step S26; see FIG. 6(C)). As a result, the endoscopic device 34 is guided by the guide wire 33 and inserted into the bile duct BD with the grasping portion 34A at the head.

Figure 8:
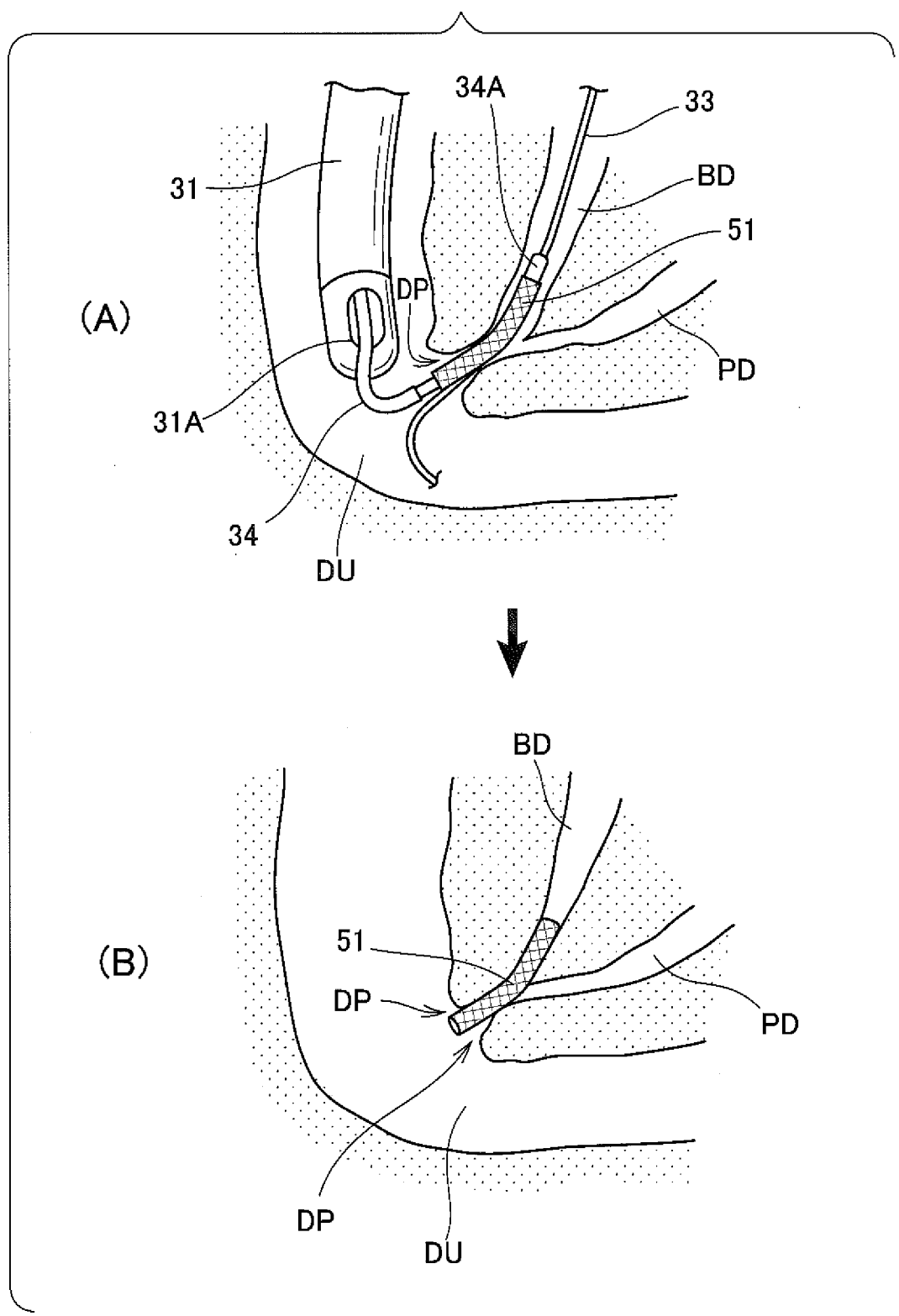
FIG. 8 is a diagram for explaining insertion of an indwelt object in the variation example.

In this method (Step S21 to Step S26), when an indwelt object 51, such as a stent, is detachably attached to the endoscopic device 34 in advance, in a manner similar to that in FIG. 8(A), which is related to a variation example described hereafter, the indwelt object 51 can be inserted into the papilla DP (or the anastomotic site) together with the endoscopic device 34. As shown in FIG. 8(B), the indwelt object 51, such as a stent, can be easily indwelt in the papilla DP or the like (Step S27).

When the step (procedure) for indwelling the indwelt object 51 such as this is completed, the endoscopic device 34 and the guide wire 33 are removed (Step S28).

Variation Example

Figure 7:
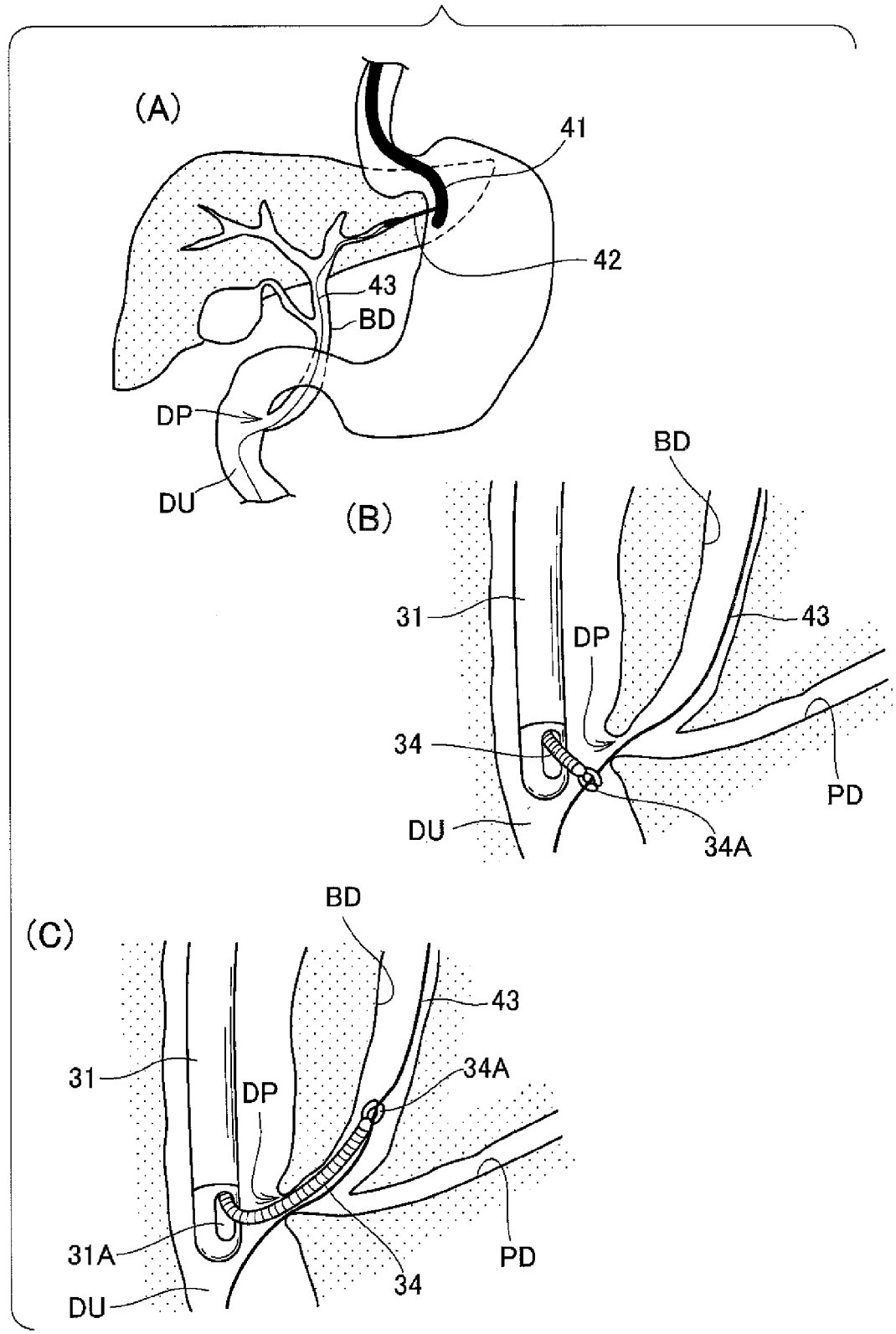
FIG. 7 is a diagram for explaining the method for inserting an endoscopic device in a variation example of the second example.

A variation example of the above-described second example will be described with reference to FIG. 7. In the variation example, the second example is used in a bile duct procedure referred to as a rendezvous method, under ultrasonic endoscope. The rendezvous method is performed for difficult ERCP cases and is referred to as an endoscopic ultrasound (EUS) rendezvous method (refer to Vinay Dhir et al., "EUS-guided bile rendezvous using a short hydrophilic guide wire", J Interv Gastroenterol 1:4, 153-159; October/November/December 2011; ©2011 Landes Bioscience).

First, an ultrasound image is acquired by scanning performed by an ultrasound endoscope 41 that is inserted into the gastrointestinal tract. The ultrasound image delineates the bile duct BD. While viewing the image, the operator punctures the bile duct BD with a puncture needle 42. As shown in FIG. 7(A), the bile duct to be punctured may be an intrahepatic bile duct. Alternatively, the bile duct may be an extrahepatic bile duct (not shown). When the intrahepatic bile duct is punctured, puncturing is performed from the stomach or the esophagus. When the extrahepatic bile duct is punctured, puncturing is performed from the duodenum.

Next, the operator passes the guide wire 43 through the puncture needle 42 until the tip portion of the guide wire 43 reaches the duodenum DU, via the papilla DP. As a result, as shown in FIG. 7(A), the guide wire 43 passes through the bile duct BD. Furthermore, the guide wire 43 is indwelt in a state in which the tip portion of the guide wire 43 projects into the internal space of the duodenum DU from the papilla DP.

Next, the operator removes the ultrasonic endoscope. In a manner similar to that in the above-described second example, the operator inserts the endoscope 31 for the duodenum into the duodenum DU. Subsequently, the operator similarly performs the above-described processes at Step S24 in FIG. 5 and subsequent steps, such as inserting the endoscopic device 34 into the channel 31A of the endoscope 31, grasping the guide wire 43 that projects from the papilla DP with the grasping portion 34A of the endoscopic device 34, and inserting the endoscopic device 34 that is guided by the guide wire 43 into the bile duct BD.

When the indwelt object 51, such as a stent, is detachably attached to the endoscopic device 34 in advance, as shown in FIG. 8(A), the indwelt object 51 can be inserted into the papilla DP (or the anastomotic site) together with the endoscopic device 34. Therefore, as shown in FIG. 8(B), the indwelt object 51, such as a stent, can be easily indwelt in the papilla DP or the like.

After completion of the step (procedure) for indwelling the indwelt object 51 as described above, fixing of the guide wire 43 by the endoscopic device 34 is released. The endoscopic device 34 is removed outside of the body.

The endoscopic device 34 may be used together with a guide sheath in by a method similar to that in the variation example according to the first embodiment. As a result, the tip portion of the guide wire 71 can be indwelt in the first hollow organ TT1 (such as the bile duct). Alternatively, a contrast agent can be injected into the bile duct or the like through the second lumen.

Third Example

Next, the method for inserting an endoscopic device according to a third example will be described with reference to FIG. 9 and FIG. 10. The insertion method is applied to a procedure referred to as pancreatic pseudocyst drainage.

Figure 9:
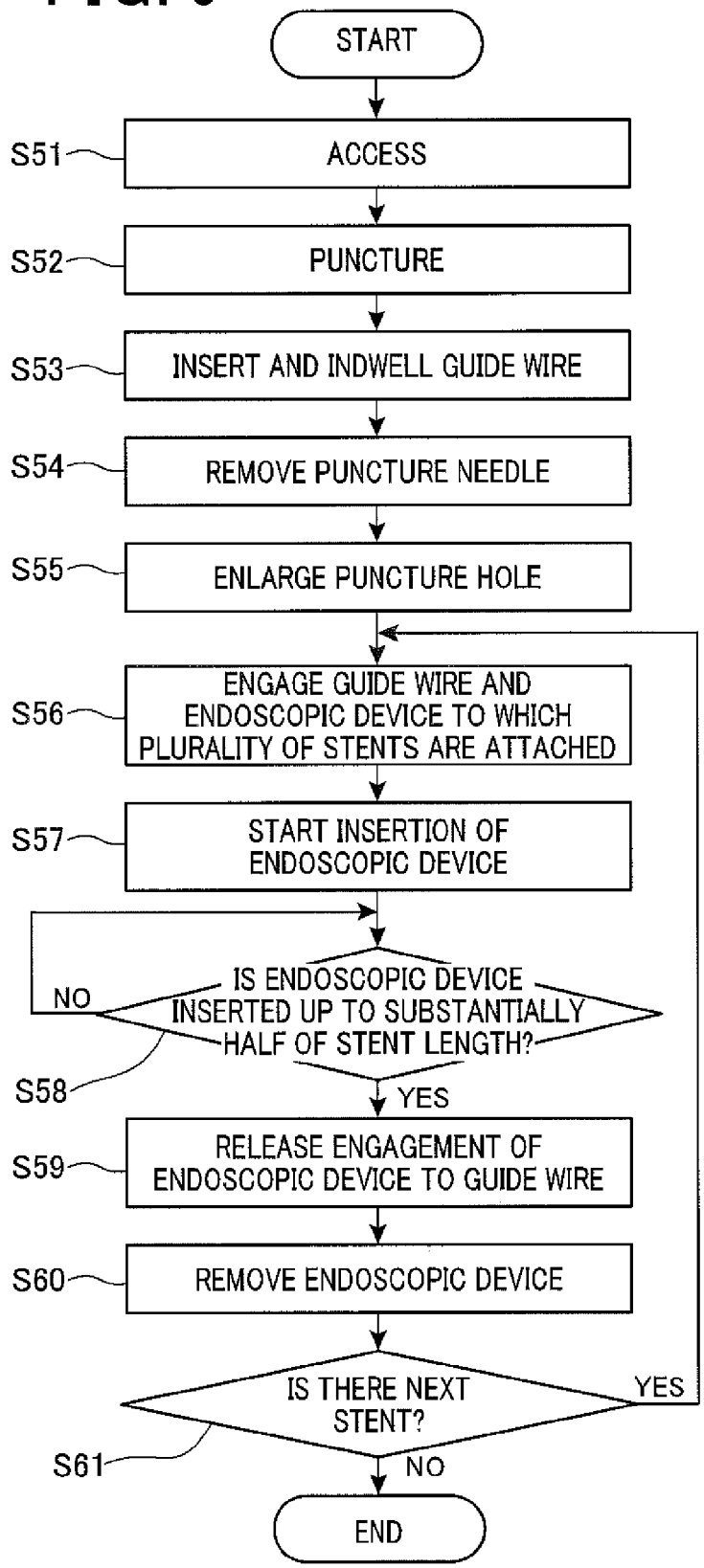
FIG. 9 is a flowchart for explaining the method for inserting an endoscopic device in a third example of the present invention.
Figure 10:
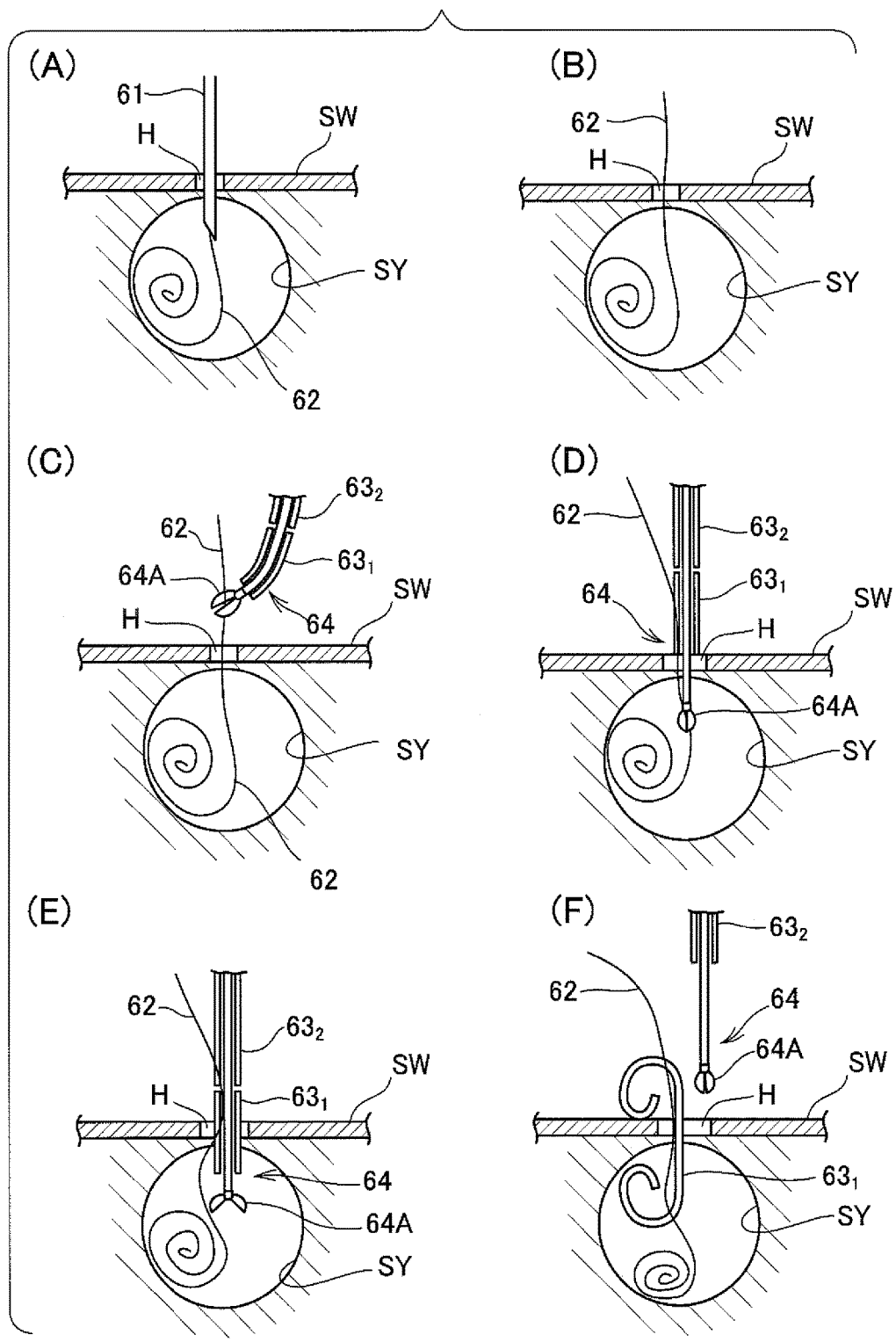
FIG. 10 is a diagram for explaining the insertion method in the third example.

First, as an example, the operator inserts an endoscope into the stomach (Step S51 in FIG. 9). The operator then punctures a cyst CY from the stomach wall SW using a puncture needle 61 (Step S52). Next, the operator inserts a guide wire 62 through the lumen of the puncture needle 61. The operator indwells the guide wire 62 so as to be positioned inside and outside the cyst CY (Step S53; see FIG. 10(A)). Next, the operator removes only the puncture needle 61, thereby leaving the guide wire 62 indwelt as is (Step S54; see FIG. 10(B)).

Subsequently, the operator enlarges the diameter of a hole H (puncture hole) that is punctured into the stomach wall SW (Step S55). To enlarge the diameter, a dilation catheter, a balloon catheter, a diathermic sheath, or the like that is inserted through the channel of the endoscope is used (not shown).

Next, the operator inserts an endoscopic device 64 (such as grasping forceps) into the channel of the endoscope (not shown). A plurality of stents 63 are detachably attached to the outside of the tip end portion of the endoscopic device 64. The operator engages a grasping portion 64A of the endoscopic device 64 with a portion of the guide wire 62 that projects outside of the stomach wall hole H inside the body, while viewing an endoscopic image (Step S56; see FIG. 10(C)). Specifically, when the grasping portion 64A is hooked forceps, the guide wire 62 is inserted with play into a space formed between the forceps in a closed state.

When the foregoing operation is completed, the operator starts to push forward the endoscopic device 64 with the grasping portion 64A at the head, along the guide wire 62 to which the endoscopic device 64 is engaged (Step S57; see FIG. 10(D)). The operator advances the endoscopic device 64 while checking whether or not substantially half of a first stent has entered the cyst CY (Step S58). When substantially half of the first stent has entered the cyst CY as shown in FIG. 10(E), the operator stops advancing the endoscopic device 64. The operator operates the endoscopic device 64 and makes the grasping portion 64A release the guide wire 62 (Step S59).

Subsequently, the operator temporarily removes the freed endoscopic device 64 from the cyst CY. As a result, as shown in FIG. 10(F), the first stent 63 is also freed from external force. The first stent 63 returns to a shape that is remembered in advance. The first stent 63 is indwelt so as to connect the cyst CY and the outer side of the stomach wall SW (in other words, inside the stomach).

When a stent 63 that has not been indwelt remains, the operator returns the operating steps to Step S56. The operator then similarly indwells the next stent 63 in a manner similar to that described above (Step S61). As a result, the plurality of stents 63 are indwelt so as to connect a single cyst CY and the inside of the stomach.

When indwelling of all stents 63 is completed, the guide wire 62 is also removed from the cyst CY (Step S62). When a plurality of cysts CY are present, the drainage procedure is performed for each cyst CY.

In a conventional method, when a plurality of stents are indwelt, a stent delivery system is required to be inserted and removed through a guide wire each time a stent is indwelt. Alternatively, a number of guide wires amounting to the number of stents is required to be indwelt. In the pancreatic pseudocyst drainage as well, the plurality of stents 63 can be successively indwelt using the single guide wire 62 that is indwelt once. During the indwelling operation, the single guide wire 62 can naturally provide a guide function for a plurality of endoscopic device insertion operations. Therefore, the endoscopic devices are not required to be inserted and removed through the guide wire. As a result, a collaborative operation related to the insertion of an endoscopic device that is performed with an assistant becomes unnecessary. The technique can be simplified and performed in less time.

What is claimed is:

1. A method for inserting an endoscopic device into a hollow organ, comprising:
   a first step of inserting a guide wire from a first hollow organ towards a second hollow organ, the first hollow organ communicating with the second hollow organ;
   a second step of positioning the guide wire such that the guide wire passes through the first hollow organ and partly protrudes from the first hollow organ into the second hollow organ, a protruded head-side portion of the guide wire which protrudes from the first hollow organ being defined as a first section, and a remaining portion of the guide wire which remains in the first hollow organ being defined as a second section;
   a third step of making an endoscopic device slidably engage with the first section of the guide wire so as to provide the endoscopic device with an engaged portion in the second hollow organ, the endoscopic device being positioned in the second hollow organ via a channel of an endoscope; and
   a fourth step of pushing the endoscopic device along the guide wire so as to move the engaged portion from the first section to the second section remaining in the first hollow organ, during which the guide wire is positionally held in a state provided by the second step.

2. The method of claim 1, comprising
   a fifth step of inserting a second guide wire from second hollow organ to the first hollow organ via the endoscope, during which a state where the engaged portion has been moved in the first hollow organ by the fourth step is maintained.

3. The method of claim 2, wherein
   the fifth step comprises a step of locating a guide sheath in the first hollow along the endoscopic device and inserting the second guide wire via the guide sheath.

4. The method of claim 2, wherein
   the second guide wire is inserted from second hollow organ to the first hollow organ in the fifth step.

5. The method of claim 1, comprising:
   a sixth step of releasing the endoscopic device from engaging with the guide wire; and
   a seventh step of pulling out the released endoscopic device from outside the subject.

* * * * *